US 8,252,295 B2

(12) United States Patent
Engstad et al.

(10) Patent No.: US 8,252,295 B2
(45) Date of Patent: *Aug. 28, 2012

(54) ENZYME TREATMENT OF GLUCANS

(76) Inventors: Rolf Engstad, Tromsø (NO); Finn Kortner, Tromsø (NO); Borre Robertsen, Tromsø (NO); Gunnar Rorstad, Tromsø (NO)

(*) Notice: Subject to any disclaimer, the term of this patent is extended or adjusted under 35 U.S.C. 154(b) by 0 days.

This patent is subject to a terminal disclaimer.

(21) Appl. No.: 12/978,923

(22) Filed: Dec. 27, 2010

(65) Prior Publication Data

US 2011/0104208 A1  May 5, 2011

Related U.S. Application Data

(63) Continuation of application No. 11/093,427, filed on Mar. 30, 2005, now Pat. No. 7,883,875, which is a continuation of application No. 08/716,344, filed as application No. PCT/IB95/00265 on Apr. 18, 1995, now abandoned.

(51) Int. Cl.
*A61K 39/00* (2006.01)
(52) U.S. Cl. .................. 424/274.1; 424/184.1; 435/101; 514/54
(58) Field of Classification Search .......................... None
See application file for complete search history.

(56) References Cited

U.S. PATENT DOCUMENTS

| | | | |
|---|---|---|---|
| 3,954,979 A | 5/1976 | Bowman |
| 4,707,471 A | 11/1987 | Larm et al. |
| 4,810,646 A | 3/1989 | Jamas et al. |
| 4,992,540 A | 2/1991 | Jamas et al. |
| 5,028,703 A | 7/1991 | Jamas et al. |
| 5,057,503 A | 10/1991 | Czop et al. |
| 5,082,936 A | 1/1992 | Jamas et al. |
| 5,147,862 A | 9/1992 | Niki et al. |
| 5,401,727 A | 3/1995 | Rorstad et al. |
| 5,488,040 A | 1/1996 | Jamas et al. |
| 5,532,223 A | 7/1996 | Jamas et al. |
| 5,817,643 A | 10/1998 | Jamas et al. |
| 5,849,720 A | 12/1998 | Jamas et al. |
| 6,020,324 A | 2/2000 | Jamas et al. |
| 2005/0255565 A1 | 11/2005 | Engstad et al. |

OTHER PUBLICATIONS

Office Action for U.S. Appl. No. 11/951,811, dated Dec. 11, 2009.

*Primary Examiner* — Kade Ariani

(57) ABSTRACT

β-(1-6)-Glucanese treatment of glucan from yeast cells, pure or feed grade, especially yeast from the family *Saccharomyces* and particularly *Saccharomyces cerevisiae*, provides a novel glucan product suitable for use in enhancing the stimulation of host animal immune systems. Solubilization of such yeast cell glucan is further disclosed to extend the usefulness of yeast cell glucan as an adjuvant.

9 Claims, No Drawings

ENZYME TREATMENT OF GLUCANS

This application is a continuation of U.S. Ser. No. 11/093,427, filed Mar. 30, 2005, which is a continuation of U.S. Ser. No. 08/716,344, filed Nov. 26, 1996, now abandoned, which was a filing under 35 USC 371 of PCT/IB95/00265, filed Apr. 18, 1995, which claims priority from Norway Application No. 94.1581, filed Apr. 29, 1994. These prior applications are incorporated herein by reference.

This invention relates to the structural modification of yeast glucans, especially but not exclusively from the family *Saccharomyces*, by using β-(1-6)-glucanase, and the use of such modified glucans in vaccine and animal feed formulations.

BACKGROUND OF THE INVENTION

It is known from European Patent Application Ser. No. 91111-143.3 (Publication No. 0466031 A2) that the immune system of aquatic animals can be stimulated through the administering of an effective amount of a yeast cell wall glucan. It is further known that the effect of vaccines on such aquatic animals can be enhanced by the administering of an effective amount of such yeast cell wall glucan along with the vaccine antigens.

Such glucan compositions are particulate glucans such as that derived from the yeast *Saccharomyces cerevisiae*. Such particulate glucans are macromolecular and are comprised of a chain of glucose units linked by β-(1-3)- and β-(1-6)-linkages, said glucan being a branched β-(1,3)-glucan having β-(1,3)-linked and β-(1,6)-linked chains therein.

Such particulate glucans are provided by KS Biotec-Mackzymal under the brand "MacroGard" and are potent activators of the macrophage/monocyte cell series. Thus such particulate glucans have a profound effect on the immune system.

While the particulate glucan derived from *Saccharomyces cerevisiae* is recognized to have a variety of beneficial effects on fish and other animals, the use of the glucan in the particulate and thus insoluble form is limited.

In addition it is now believed that the presence of β-(1-3)-branches contribute to the desired pharmaceutical benefits to be obtained from particulate glucan.

Accordingly a system whereby the β-(1-3)-linked branches are made more readily available in the glucan would be highly desirable.

SUMMARY OF THE INVENTION

In accordance with the present invention it has been discovered that by treating the particulate glucan derived from yeast organisms, especially of the family *Saccharomyces*, and particularly *Saccharomyces cerevisiae*, with a β-(1-6)-glucanase, there is obtained a modified particulate glucan which is characterized by its enhanced activity in effecting stimulation of the immune system.

Thus in one embodiment of the present invention there is provided a novel β-(1-3)-glucan from yeast which is characterized by its enhanced ability to stimulate the immune system of fish and other animals.

In another embodiment of this invention there is provided a novel process for the production of β-(1-3)-glucan from yeast having enhanced pharmaceutical activity.

In another embodiment of this invention there is provided a novel solubilized β-(1-3)-glucan from yeast which is useful for enhancing the activity of veterinary vaccines.

In still another embodiment of the present invention there is provided a novel feed grade glucan composition which is useful as an ingredient in conventional animal feeds.

Other embodiments and advantages of this invention will be apparent from the following specifications and claims.

Process for Preparation of β-(1-6)-Glucanase Treated Glucan ("MacroGard").

"MacroGard" brand glucan is derived from *Saccharomyces cerevisiae* as disclosed in European Application Ser. No. 91111143.3. While such glucan is known to stimulate the immune system of fish, according to a preferred embodiment of the present invention, its activity is enhanced by the treatment thereof with a β-(1-6)-glucanase.

Such glucanase treatment of the glucan is carried out by suspending the glucan particle in a buffered medium at a pH in the range of about 4 to about 8 and at a temperature in the range of from about 20 to about 50° C. Suitable buffered media are those selected from the group consisting of sodium acetate, ammonium acetate and sodium-potassium phosphate. Presently preferred buffer solutions are sodium acetate or ammonium acetate. Enzymatic degradation of the glucan is commenced by the addition of the β-(1-6)-glucanase to the buffered medium.

β-(1-6)-glucanases which are suitable for the modification of yeast glucan in accordance with the present invention are those obtained from a microorganism selected from the group consisting of *Trichoderma longibrachiatum*, *Trichoderma reesei*, *Trichoderma harzianum*, *Rhizopus chinensis*, *Gibberella fuiikuroi*, *Bacillus circulans*, *Mucor lilmalis*, and *Acinetobacter*. Of these a presently preferred glucanase is that obtained from *Trichoderma harzianum*.

The amount of β-(1-6)-glucanase employed for treatment of the glucan is normally in the range of from 1 to 50 U per g of glucan.

Enzymatic degradation is terminated by heating the reaction mixture to a temperature in the range of 80 to 100° C., preferably for a time in the range of 2 to 10 min. Other ways to stop the enzyme degradation are, e.g. by adding proteases or inhibitors to the reaction mixture.

Alternatively the enzyme may be simply removed by washing. The washed particles are then resuspended in water with the addition of a bactericide such as 0.3% formalin (v/v) and stored at a temperature of about 4° C.

The resulting enzyme treated glucan can be characterized as a branched β-(1-3)-glucan with β-(1-3)-linked sidechains being attached by a β-(1-6)-linkage and being essentially free of β-(1-6)-linked chains. In this connection the phraze "β(1-6) chains" is meant to include branches of more than 1β(1-6)-linked glucose units. The β-(1-6)-glucanase enzyme cleavage ensures that most chains of more than 4β-(1-6)-bound glucose units are cleaved off.

To further enhance the utility of the glucan, it is subject to solubilization. Such solubilization treatment is generally carried out at a temperature in the range of about from 70 to 90° C. for a period of from about 30 to 60 min in the presence of a solubilizing agent. A presently preferred solubilizing agent is formic acid. Following solubilization the solubilizing agent is removed and the resulting glucan is boiled in distilled water.

In practicing the present invention glucan can be first enzyme treated and then solubilized or conversely be solubilized and then enzyme treated.

In accordance with another embodiment of this invention there is provided a β-(1-6)-glucanase treated feed grade glucan from yeast, e.g. *Saccharomyces cerevisiae*. Such feed grade glucan can be obtained by first contacting the yeast cell wall with an aqueous alkaline solution under conditions to effect the extraction of proteins and lipids therefrom. Generally such extraction is carried out at a temperature in the range from about 50 to 80° C. for about 2 to 8 h. A presently preferred alkaline extraction agent is sodium hydroxide. Following extraction, the cell walls are recovered from the aqueous alkaline solution and washed to remove solubilized cell wall components therefrom. The washed yeast cell wall are then neutralized by treatment with an acid such as phosphoric acid. Thereafter the neutralized washed glucan is pasteurized and then dried.

Suitable enzymes for treatment of the feed grade glucan are those useful in treating the high purity glucan.

The enzyme treated feed grade glucan is prepared by contacting the glucan with a β-(1-6)-glucanase in the same manner as that employed to the enzyme treatment of the glucan particulate. The β-(1-6)-glucanase treated feed grade glucan of this invention is useful in animal feed formulations.

The following examples are presented for purposes of illustration of the invention.

EXAMPLE 1

This example provides the protocol used to obtain an immunostimulatory glucan particle suitable for utilization in the practice of the present invention.

500 g of dry *Saccharomyces cerevisiae* was suspended in 3 l of 6% aqueous NaOH solution. This suspension was then stirred overnight at room temperature. After stirring the suspension was centrifuged at 2000×g for 25 min. The supernatant was discarded and the insoluble residue was then resuspended in 3 l of 3% NaOH and incubated for 3 h at 75° C. followed by cooling the suspension overnight. The suspension was then centrifuged at 2000×g for 25 min and the supernatant was is decanted. The residue was then resuspended in 3% NaOH, heated and centrifuged as previously described.

The insoluble residue remaining was then adjusted to pH 4.5 with acetic acid. The insoluble residue was then washed with 2 l of water three times and recovered by centrifuging at 2000×g for 25 min. after each wash (the supernatant was poured off). The residue was then suspended in 3 l of a 0.5 M aqueous acetic acid. The suspension was heated for 3 h at 90° C. The suspension was then cooled to room temperature. After cooling, the insoluble residue was then collected by centrifuging at 2000×g for 25 min. This treatment (from adjusting to pH 4.5 to collecting the cooled residue) was repeated 6 times.

The insoluble residue was then suspended in 3 l of distilled water and stirred for 30 min at 100° C., then cooled and centrifuged at 2000×g for 25 min. The supernatant was discarded. The insoluble residue was washed in this manner 4 times. The residue was next suspended in 2 l of ethanol and heated at 78° C. for 2 h. This wash with ethanol was repeated 4 times. The residue was then washed 4 times with 3 l of distilled water at room temperature to remove the ethanol, thereby providing a suspension of desired glucan product.

EXAMPLE 2

This example provides the protocol to obtain glucan particles essentially free of β-(1-6)-linked chains with the use of β-(1-6)-glucanase isolated from *Trichoderma harzianum*.

200 mg of glucan particles prepared in accordance with Example 1 were suspended in 40 ml 50 mM ammonium acetate buffer, pH 5.0, together with 10 U of β-(1-6)-glucanase at 37° C. for 6 h with constant stirring. The enzymatic degradation of the glucan particles was ended by heating the suspension at 100° C. for 5 min. The particles were then washed three times with 200 ml sterile distilled $H_2O$ by centrifugation at 2000×g for 10 min, whereafter 185 mg of dried enzyme treated glucan was obtained.

The enzyme treatment will only cleave β-(1-6)-linkages within β-(1-6)-linked chains, but will not remove the β-(1-6)-linked glucosyl residue extending from the branching points. The resulting enzyme treated glucan can be characterized as a branched β-(1-3)-glucan with β-(1-3)-linked sidechains being attached by a β-(1-6)-linkage and being essentially free of β-(1-6)-linked chains.

EXAMPLE 3

This example provides the protocol to solubilize glucan particles prepared in accordance with Example 1 by hydrolysis using formic acid (HCOOH).

2.0 g of glucan particles were suspended in 1.0 l of 90% formic acid and heated at 80° C. for 45 min under constant stirring. The suspension was cooled to 35° C. and the formic acid was evaporated. The residue containing the hydrolysed particles was boiled in 500 ml distilled water for 3 h, whereafter the cooled suspension was filtrated through a 0.44 μm filter, frozen and lyophilized whereby 1.9 g of dry solubilized particles were obtained. The lyophilized solubilized particles were then dissolved in 100 ml distilled water and dialyzed, using a tubular dialysis membrane having a nominal molecular weight cut off (NMWCO) of 5000 Dalton, against tap water for 24 h, and then lyophilized. This resulted in 1.8 g solubilized glucan product.

EXAMPLE 4

This example demonstrates the biological effects of glucan particles prepared according to Example 1, and β-(1-6)-glucanase treated glucan particles prepared according to Example 2 on immune responses in Atlantic salmon.

An A-layer positive isolate of *Aeromonas salmonicida* subsp. *salmonicida*, referred to as strain no. 3175/88 (Vikan Veterinary Fish Research Station, Namsos, Norway) was used. The bacterium was grown in brain heart infusion broth (Difco, USA) for 30 h at 14° C. in a shaker incubator, and the culture medium with the bacterium was centrifuged for 10 min at 3000×g. The pellet was resuspended in 0.9% saline, and the bacterium was killed by adding 0.5% formalin (v/v) to the suspension and incubating at 14° C. for 24 h. The formalinized culture was then washed with sterile 0.9% saline and resuspended to a concentration of $2 \times 10^9$ $ml^{-1}$ bacteria in 0.9% saline with 0.3% formalin. Bacterial suspensions were mixed with an equal volume of saline or with the different glucan suspensions (10 mg $ml^{-1}$ in saline). Formalin was added to the vaccines to a final concentration of 0.3% (v/v).

In carrying out these experiments, two groups of experimental fish were used. In the vaccine experiment, Atlantic salmon presmolts of 20-40 g were used. In the experiment where serum was collected for measuring blood lysozyme activity after glucan injection, Atlantic salmons of 50-70 g were used. The fish were kept in 150 l tanks supplied with aerated fresh water at 12° C. and fed with commercial pellets ad libitum twice daily.

In the vaccination experiment 40 fish in each group were IP-injected with 0.1 ml of the different vaccine preparations or vaccine without glucan as a control. Blood was collected in evacuated tubes (Venoject, Terumo-Europe, Belgium) from 10 fish in each group 6, 10, and 18 weeks after injection. Blood samples were allowed to clot overnight at 4° C. and sera were collected after centrifuging the tubes at 2000×g for 10 min. Individual serum samples were transferred to Micronic serum tubes (Flow Laboratories Ltd., Lugano, Switzerland) and stored at −80° C. until required.

In order to measure the effect of glucans on blood lysozyme activity, salmons were IP injected with 0.3 ml of the different glucans in saline or with 0.3 ml saline as the negative control. The glucans were administered at a concentration of 10 mg ml$^{-1}$. Blood samples were collected from 10 fish from each group 10 and 20 days after injection, using evacuated tubes (Venoject). The tubes were kept on ice until centrifuged at 2000×g for 10 min, and individual serum samples were transferred to Micronic serum tubes and stored at −80° C. until required.

Lysozyme activity was measured with the turbidimetric method using 0.2 mg ml$^{-1}$ lyophilized *Micrococcus lysodeikticus* as the substrate in 0.04 M sodium phosphate buffer at pH 5.75. Serum (20 µl) was added to 3 ml of the suspension and the reduction in absorbance at 540 nm was measured after 0.5 min and 4.5 min at 22° C. One unit of lysozyme activity was defined as a reduction in absorbance of 0.001 min$^{-1}$. Results are expressed as mean lysozyme activity in serum from 10 fish (Tables 1 and 2).

The level of specific antibody against the A-layer of *A. salmonicida* in salmon sera was measured by an enzyme-linked immunosorbent assay (ELISA). A-layer protein was purified from whole *A. salmonicida* cells (Bjørnsdottir et al. (1992), *Journal of Fish Diseases*, 15:105-118), and protein content was determined (Bradford, M. M. (1976), *Analytical Biochemistry*, 72:248-254) using a dye-reagent concentrate from Bio-Rad Laboratories (Richmont, USA). Microtitre plates were coated with 100 µl of 5 µg ml$^{-1}$ A-layer protein in 50 mM carbonate buffer, pH 9.6, and incubated overnight at 4° C. The further procedure was performed as described by Håvardstein et al. (*Journal of Fish Diseases* (1990), 13:101-111). The antibody titre in pooled serum samples was determined before individual serum samples were measured at three different dilutions (1:500, 1:1000 and 1:2000). Absorbance was read at 492 nm in a Multiscan MCC/340 MK II (Flow Laboratories Ltd). Results are expressed as mean antibody response to the A-layer of the bacterium at a dilution of 1:2000 in serum from 10 fish (Tables 1 and 2).

TABLE 1

Differences in biological effects of glucan particles and β-(1-6)-glucanase treated glucan particles on immune responses in Atlantic salmon.

| Lysozyme activity Post injection (units/ml) | Saline Control | Untreated glucan particles | β-(1,6)-glucanase) treated glucan Particles |
|---|---|---|---|
| 10 days | 304 | 505 | 529 |
| 20 days | 330 | 407 | 454 |

| Antibody response Post injection (absorbance) | Vaccine without glucan | Vaccine with untreated glucan particles | Vaccine with β-(1,6)-glucanse treated glucan particles |
|---|---|---|---|
| 6 weeks | 0.165 | 0.255 | 0.376 |
| 10 weeks | 0.059 | 0.355 | 0.500 |
| 18 weeks | 0.037 | 0.197 | 0.142 |

Both injection of untreated and β-(1,6)-glucanase treated glucan particles induced significantly higher (p<0.01) lysozyme activity in serum compared to saline control both 10 and 20 days post injection. At day 20 post injection the lysozyme levels in fish injected with β-(1,6)-glucanase treated glucan particles were significantly higher (p<0.05) compared to fish injected with untreated particles.

β-(1,6)-glucanase treated glucan particles induced significantly higher (p<0.05) antibody response to the vaccine compared to vaccine without adjuvant at all three sampling times, whereas untreated glucan particles induced significantly higher response 10 and 18 weeks post injection. S-(1,6)-glucanase treated glucan particles induced significantly higher (p<0.05) antibody response than did untreated glucan particles at 10 weeks post injection, whereas no significant differences between the two were observed at 6 and 18 weeks post injection.

TABLE 2

Biological effects of glucan particles and solubilized glucan.

| Lysozyme activity (units/ml) | Saline Control | Untreated glucan particles | Solubilized glucan particles |
|---|---|---|---|
| 10 days after injection | 304 | 505 | 603 |
| 20 days after injection | 330 | 407 | 773 |

| Adjuvant effect (absorbance) | Vaccine without glucan | Vaccine with untreated glucan particles | Vaccine with solubilized glucan particles |
|---|---|---|---|
| 6 weeks after injection | 0.165 | 0.255 | 0.184 |
| 10 weeks after injection | 0.059 | 0.355 | 0.349 |
| 18 weeks after injection | 0.037 | 0.197 | 0.120 |

Injection of solubilized glucan particles induced significant higher (p<0.01) lysozyme activity than did untreated glucan particles both 10 and 20 days post injection. No significant differences could be observed between the ability of solubilized glucan particles and untreated glucan particles to induce increased antibody response to the vaccine antigen at any sampling time point. Both induced significant higher (p<0.05) antibody response than vaccine without adjuvant 10 and 18 weeks post injection, but not at 3 weeks post injection.

EXAMPLE 5

This example provides the protocol to obtain a glucan composition suitable for use in the feeding of animals.

1000 kg of dry cell wall material of *Saccharomyces cerevisiae* was suspended in 5300 l of water at a temperature of 65° C. in a stainless steel tank. To the suspension of cell walls in water there was added 227 l of 50% w/w NaOH so as to provide a caustic concentration of about 3%. The resulting mixture was then stirred for a period of about 4 h at a temperature of about 60° C.

Following the initial extraction period the suspension was then diluted with 8000 kg of water at a temperature of about 65° C. in a stainless steel, stirred, washing tank such that the weight of the mixture was doubled. The resulting diluted mixture was then maintained at a temperature of about 60° C. while being stirred for a period of about 15 min. Thereafter the resulting mixed diluted suspension was centrifuged in a nozzle centrifuge (Alfa Laval DX209). The supernatant was discarded. The resulting concentrated cell wall suspension was continuously introduced into a second steel stirred wash tank containing 8000 kg water and the mixture adjusted by the addition of water to give a final weight of 0.14500 kg. The resulting suspension was then mixed for a period of 15 min at a temperature of 60-65° C. Thereafter the agitated mixture was centrifuged.

The resulting cell wall suspension was continuously added to a third vessel containing 8000 kg water. Additional water at 60° C. was added to provide a final weight of 14500 kg. The resulting suspension was stirred for a period of 15 min at 60-65° C. and thereafter centrifuged.

Following centrifugation, the resulting cell wall concentrate was transferred to a stainless steel storage tank wherein the suspension was cooled to a temperature of about 5-10° C. The resulting cooled suspension was treated with phosphoric acid ($H_3PO_4$) in a stainless steel agitated tank in an amount to achieve a suspension of solids having a pH of 5.5-7.5.

Following neutralization the resulting neutralized mixture was subjected to pasteurization by heating at a temperature of 75° C. for a period of 18 seconds by passing the mixture through an in-line plate and frame heat exchanger.

Following pasteurization the resulting pasteurized mixture was then spray dried in a spray drier maintained at an inlet air temperature of at least 140-150° C. and an exhaust temperature of about 65-70° C. whereby there was achieved 300 kg of dry glucan product.

EXAMPLE 6

This example provides the protocol and effect of treatment of feed grade glucan with a S-(1-6)-glucanase.

25 g of feed grade glucan, prepared in accordance with Example 5, suspended in 1.25 l of 50 mM sodium acetate, pH 5.0, in a 2 l conical flask. Glucan particles were maintained in suspension by shaking, the suspension was warmed to 30° C. and purified S-(1-6)-glucanase from *Trichoderma harzianum* was added to a final concentration of 1.8 U/g glucan.

To follow the timecourse of the enzymatic removal of β-1,6-bound glucose from the glucan particle, 1 ml aliquots of the suspension were withdrawn at different timepoints, centrifuged at 2000×g, and 0.2 ml of the supernatants analyzed for free, reducing carbohydrate (Nelson et al. (1944), *Journal of Biological Chemistry*, 153:315-80). The glucan suspension was incubated for 28 h at which time the rate of release of free, reducing carbohydrate was observed to be very low. The glucan particles were then pelleted by centrifugation at 2000×g, washed once in 50 mM sodium-acetate, pH 5.0 and once in water.

A fine, dry powder suitable for use as a feed additive was prepared from the wet glucan by first dehydrating the pellet four times with ethanol at room temperature followed by air drying at room temperature.

Results from treating a feed grade glucan with β-(1-6)-glucanase from *T. harzianum* as described above are shown in Table 3.

TABLE 3

Liberation of glucose from feed grade glucan during treatment with β-(1-6)-glucanase from *T. harzianum*.

| Enzyme reaction time, (h) | Glucose liberated, (% of total glucose in glucan) |
|---|---|
| 0 | 0.0 |
| 0.5 | 1.9 |
| 1 | 2.6 |
| 2 | 3.3 |
| 3 | 3.7 |
| 4 | 4.0 |
| 5 | 4.3 |
| 2 | 5.5 |
| 8 | 5.6 |

What is claimed is:

1. A method of increasing immunostimulation in animals by administering to the animal a glucan product comprising a branched β-(1,3) glucan with β-(1,3)-linked side chains, said β-(1,3)-linked side chains comprising more than one β-(1,3)-linked glucose unit and being attached by a β-(1,6)-linkage said glucan being essentially free of side chains of more than four β-(1,6)-bound glucose unit.

2. The method according to claim 1 wherein the glucan is solubilized.

3. The method according to claim 1 wherein the glucan product is in a form selected from the group consisting of a food additive, animal feed, and pharmaceutical product.

4. The method according to claim 1 wherein the glucan is derived from yeast.

5. The method according to claim 4 wherein the yeast is of the family *Saccharomyces*.

6. The method according to claim 5 wherein the yeast is *Saccharomyces cerevisiae*.

7. The method according to claim 1 wherein the glucan product is in the form of a vaccine.

8. The method according to claim 7 wherein the vaccine is administered by intraperitoneal injection.

9. The method according to claim 1 wherein the animal is a fish.

* * * * *

UNITED STATES PATENT AND TRADEMARK OFFICE
CERTIFICATE OF CORRECTION

| | | |
|---|---|---|
| PATENT NO. | : 8,252,295 B2 | Page 1 of 1 |
| APPLICATION NO. | : 12/978923 | |
| DATED | : August 28, 2012 | |
| INVENTOR(S) | : Engstad et al. | |

It is certified that error appears in the above-identified patent and that said Letters Patent is hereby corrected as shown below:

On the Title Page:

Item (30) The Foreign Application Priority Data should be added as follows:

(30)   April 29, 1994   (NO).......................94.1581

Signed and Sealed this
Sixth Day of November, 2012

David J. Kappos
*Director of the United States Patent and Trademark Office*

UNITED STATES PATENT AND TRADEMARK OFFICE
CERTIFICATE OF CORRECTION

PATENT NO. : 8,252,295 B2
APPLICATION NO. : 12/978923
DATED : August 28, 2012
INVENTOR(S) : Engstad et al.

Page 1 of 1

It is certified that error appears in the above-identified patent and that said Letters Patent is hereby corrected as shown below:

On the Title Page:

Item (73) Assignee data should be added as follows:

(73) Assignee: Biotech Pharmacon ASA, Tromso (NO)

Item (74) Attorney, Agent, or Firm information should be added as follows:

(74) *Attorney, Agent, or Firm*—Rothwell, Figg, Ernst & Manbeck

Signed and Sealed this
Twelfth Day of February, 2013

Teresa Stanek Rea
*Acting Director of the United States Patent and Trademark Office*